United States Patent [19]

Izumi

[11] Patent Number: 5,041,725
[45] Date of Patent: Aug. 20, 1991

[54] SECONDARY ION MASS SPECTROMETRY APPARATUS

[75] Inventor: Eiichi Izumi, Takahagi, Japan

[73] Assignee: Hitachi, Ltd., Tokyo, Japan

[21] Appl. No.: 553,698

[22] Filed: Jul. 18, 1990

[30] Foreign Application Priority Data

Jul. 20, 1989 [JP]  Japan .................................. 1-188200

[51] Int. Cl.⁵ ........................... H01J 37/256; H01J 49; H01J 04
[52] U.S. Cl. ..................................... 250/309; 250/288
[58] Field of Search ................................ 250/309, 288

[56] References Cited

U.S. PATENT DOCUMENTS 4,510,387  4/1985  Izumi et al. .......................... 250/309
4,874,946  10/1989  Kazmerski .......................... 250/309

Primary Examiner—Jack I. Berman
Attorney, Agent, or Firm—Antonelli, Terry, Stout & Kraus

[57] ABSTRACT

A secondary ion mass spectrometry apparatus for analyzing an element contained in the sample by radiating a primary ion beam extracted from an ion source to an analytical sample through a focusing system. The secondary ion mass spectrometry apparatus comprises an input unit for inputting data containing analytical elements names and areas, a storage unit for storing operational expressions to be operated on the input data from the input unit and a table to be reference on the input data and the results operated by the operational expressions and from which the necessary data is read, and a control unit for setting focusing conditions of said focusing system using the input data inputted from said input unit and the operational expressions and tables stored in the storage unit.

12 Claims, 7 Drawing Sheets

1

SECONDARY ION MASS SPECTROMETRY APPARATUS

BACKGROUND OF THE INVENTION

The present invention relates to a secondary ion mass spectrometry apparatus and in particular to the secondary ion mass spectrometry apparatus which employs surface mass spectrometry using ion irradiation.

This type of secondary ion mass spectrometry apparatus, as disclosed in JP-B-53-2599, takes the operating steps of irradiating primary ions to a sample surface from a primary ion source and conducting secondary ions ejected from the sample to a mass spectrometer for analyzing an impurity contained in the sample.

And, the spectrometry conditions on which this spectrometry apparatus operates have been set by a skilled operator on his or her own experience.

If, however, the operator erroneously sets the spectrometry conditions, such a spectrometry apparatus is uncapable of supplying effective data in some fields such as sensitivity, vertical resolution, and area to be analyzed (even vertically). Data analysis, therefore, requires annoying work, resulting in causing erroneous analysis or consuming meaningless time in measuring it again. Hence, the secondary ion mass spectrometry apparatus is an effective analyzing tool, though, it often seems that the apparatus requires annoying work for the data analysis. Further, how to estimate a requisite time largely depends on the skill of the operator. For example, it is necessary to determine when the spectrometry finishes based on the output data while the apparatus analyzes the sample.

The secondary ion mass spectrometry apparatus, therefore, constantly requires an operator, so that it is uneconomical. And, the apparatus has a shortcoming in that it supplies ineffective data if too short time is specified for the analysis of a sample or, as a rule, requires unnecessarily long time for the analysis if too long a time is specified.

SUMMARY OF THE INVENTION

It is, therefore, an object of the present invention to provide a secondary ion mass spectrometry apparatus which is designed to automatically set the analysis conditions for improving the analytical operation and the reproducibility of the data.

It is another object of the present invention to provide a secondary ion mass spectrometry apparatus which is capable of breaking down the restriction that more approximate output requires more working time of an operator by being able to estimate an analytical time on the analysis conditions.

To achieve the foregoing objects, the present invention is implemented by a secondary ion mass spectrometry apparatus which takes the steps of radiating a primary ion beam from an ion source to a sample material through a focusing system and performing the mass spectrometry of secondary ions ejected from the sample for analyzing impurity contained in the sample. The secondary ion mass spectrometry apparatus comprises an input unit used for inputting an analytical element name and an analytical area, a storage unit for storing a predetermined operational expression and various parameters, and a processing control unit for performing the operation and control for outputting an analysis time according to the input value of the input unit and setting the conditions of the focusing system by using the input value and the operational expressions and various parameters stored in the storage unit.

In addition to the foregoing arrangement, the secondary ion mass spectrometry apparatus according to the invention comprises means for inputting names of matrix elements and analytical impurities of the sample and means for computing a sputtering speed based on the input values, for deriving a requisite time for analysis from all the analytical elements names.

According to the arrangement, by inputting the analytical element names and areas to the input unit, the processing control unit serves to compute the most approximate analysis conditions and time and set a primary ion current, a primary ion beam diameter, and a scanning width from the computed values, resulting in being able to improve the analytical operation and the reproducibility of the data.

In addition, the invention can break down the restriction that more approximate data requires more working time of an operator.

DESCRIPTION OF THE PREFERRED EMBODIMENTS

Herein, a description will be directed to a secondary ion mass spectrometry apparatus according to an embodiment of the present invention.

Figure 1:
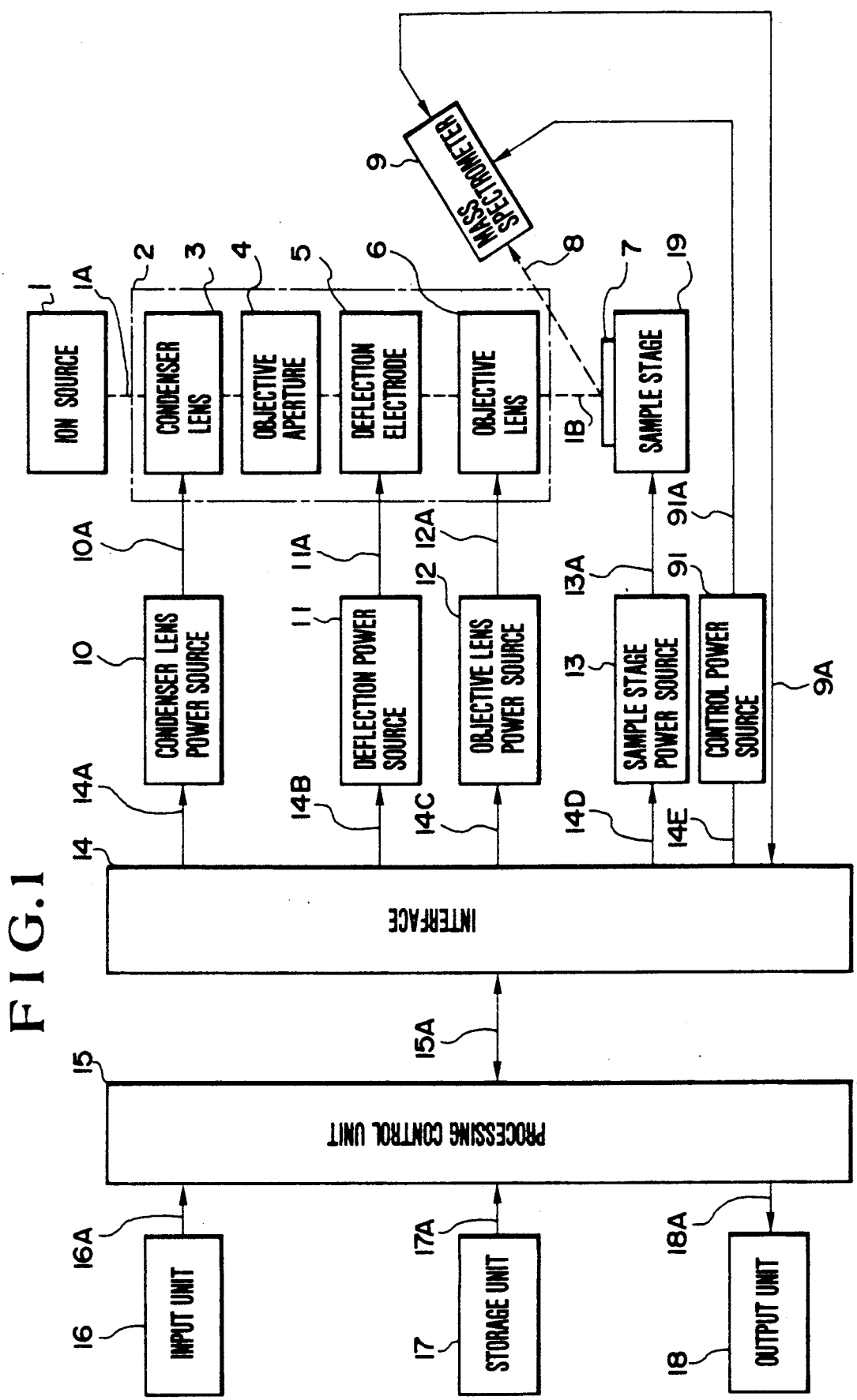
FIG. 1 is a block diagram showing a secondary ion mass spectrometry apparatus according to an embodiment of the invention.

FIG. 1 is a block diagram schematically showing the overall arrangement of the secondary ion mass spectrometry apparatus. As shown, 1 denotes an ion source, which radiates a primary ion beam 1A to a sample 7 through a focusing system 2 in which the ion beam 1A is transformed into a primary ion beam 1B with a desired beam diameter and current. As a result of the radiation of the primary ion beam 1B on the sample 7, secondary ions 8 sputtered from the sample 7 are sent to a mass spectrometer 9 in which the secondary ions 8 are analyzed into a ratio of mass to charges. The focusing system 2 consists of a condenser lens 3, an objective aperture 4, a deflecting electrode 5, and an objective lens 6 which are arranged in order from the ion source 1 to the sample 7. 15 denotes a processing control unit, which serves to derive a primary ion beam current $I_1$, a beam diameter d, a beam scanning width 1, setting conditions of the focusing system 2, and an analysis time ts based on an input signal 16A sent form an input unit 16 and a storage signal 17A from a storage unit 17.

The processing control unit 15 supplies the derived results 18A to an output unit 18. A condition-setting signal 15A of the focusing system 2 contained in the derived results 18A is supplied to some driving power sources to be described later through an interface 14 for actuating the power sources.

These driving power sources include a condenser lens deriving power source 10, a deflection power source 11, an objective lens driving power source 12, and a sample stage power source 13. The condenser lens driving power source 10 serves to apply the driving voltage 10A to the condenser lens 3 in response to a control signal 14A sent from the interface 14. The deflection power source 11 serves to apply a deflection voltage 11A to a deflection electrode 5 in response to a control signal 14B. The objective lens driving power source 12 serves to apply an objective lens voltage 12A to an objective lens 6 in response to a control signal 14C. In response to a control signal 14D, the sample stage power source 13 serves to supply a fine adjustment signal 13A so that the sample stage 19 can fine adjust the sample 7 to a desired location. These driving power sources 10 to 13 will be described later.

91 denotes a control power source, which serves to supply a selection signal 91A to the mass spectrometer 9 in response to a control signal 14E sent from the interface 14. The mass spectrometer 9 selectively detects the secondary ion having a specified ratio of mass to charges according to the selection signal. The secondary ion signal 9A detected in the mass spectrometer 9 is stored in the storage unit 17 through the interface 14 and the processing control unit 15.

Figure 2:
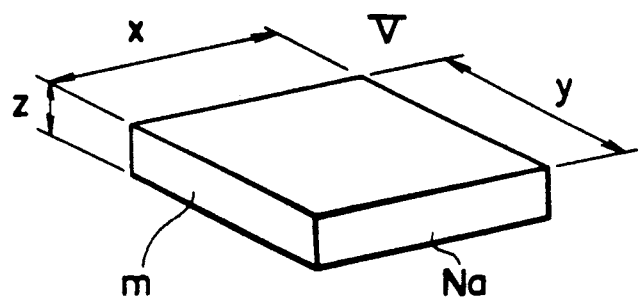
FIG. 2 is a perspective view illustrating a sample surface to be analyzed.

Next, the input signal 16A, the storage signal 17A, the derived values 18A, and the condition-setting signal 15A will be described. If the secondary ion mass spectrometer analyzes an impurity contained in the sample, a matrix element name A which is a material name of the sample 7, a name of an analytical contained in the sample 7, and an analytical area of the sample 7 are, in general, known or presumptive matters since they are analytical requisite matters. The analytical area can be represented by x, y and z as shown in FIG. 2. And, input matters to the input unit 16 are A, B, x, y, and z. In FIG. 2, V denotes a volume of the analytical area, Na denotes a sum of atoms of the matrix element A contained in the volume. It is unnecessary to input these V, Na, and m, because they can be derived on the following operational expressions by the processing control unit 15.

$$V = x \cdot y \cdot z \tag{1}$$

$$m = \rho \cdot V = \rho \cdot x \cdot y \cdot z \tag{2}$$

where $\rho$ is the density of the element A. The storage unit 17 stores as a table relation between the density and each element name, a mass number M and an Avogadro's number $6 \times 10^{23}$ of the element A.

The sum of atoms Na is $$Na = 6 \times 10^{23} \cdot m/M = 6 \times 10^{23} \cdot \rho \cdot x \cdot y \cdot z/M \tag{3}$$

Assuming that the primary ion beam current radiated on the sample is $I_1$ and the charges per ion is $1.6 \times 10^{-19}$ coulomb, the number Ni of radiated ions per square time can be represented by the operational expression $$Ni = I_1/1.6 \times 10^{-19} \tag{4}$$

When these ions are radiated on the sample, the sample atoms are subject to sputtering.

Figure 5:
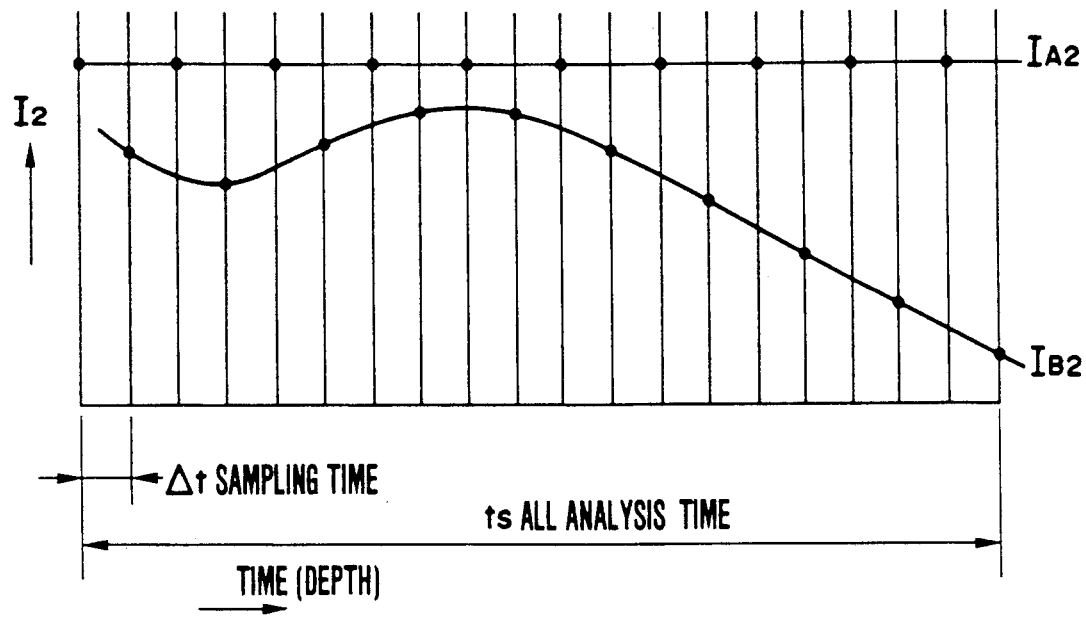
FIG. 5 is a chart illustrating relation between ion beam current and sputtering depth.

Assuming that a sputtering yield of the element A (the number of secondary ions ejected by the collision of one primary ion on the sample) is represented by Sy, Nsa denotes the number of atoms sputtered per unit time and is represented by the following expression.

$$Nsa = Sy \cdot Ni = Sy \cdot I_1/1.6 \times 10^{-19} \tag{5}$$

ts denotes a time taken when the sum of atoms Na in the analytical area of the sample is sputtered by the primary ion beam current $I_1$. The time ts is represented by the operational expressions (3), (5) and (6).

$$\begin{aligned} ts &= Na/Nsa = (6 \times 10^{23} \cdot \rho \cdot x \cdot y \cdot z/M)/ \\ &\quad (Sy \cdot I_1/1.6 \times 10^{-19}) \\ &= (6 \times 10^{23} \cdot \rho \cdot x \cdot y \cdot z \cdot 1.6 \times 10^{-19})/(M \cdot Sy \cdot I_1) \\ &= K \cdot x \cdot y \cdot z/I_1 \end{aligned} \tag{6}$$

where K is represented by $(6 \times 10^{23} \cdot \rho \cdot 1.6 \times 10^{-19})/M \cdot Sy$ in which $\rho$, M, and Sy are stored as a table in the storage unit 17. They can be derived by a simple calculation and thus are assumed to be constants. ts in the expression (6) is an analysis time required in case of inputting the sample element name A and the analytical areas x, y, z. Then, how to define the primary ion beam current $I_1$ will be described with reference to FIG. 5. FIG. 5 is a graph representing the analysis of the depth distribution of an impurity element B contained in the element A. Assuming that all the analysis time is ts and a sampling time of a detector is $\Delta t$, the secondary ion intensity is detected from each of the elements A and B at each sampling time $\Delta t$ and then are stored in the storage unit 17. In case of analyzing ts on the sampling time $\Delta t$, the sampling frequency n is represented by the operational expression:

$$n = ts/\Delta t \tag{7}$$

If the two elements are to be analyzed as shown in FIG. 5, the sampling frequency n' per element is a half of n. The too small sampling frequency n' per element results in lowering a depth profile resolution. The too large frequency n" results in reducing one sampling time, that is, a counting time of the secondary ions and reducing the counting values. It results in lowering sensitivity and narrowing a dynamic range of profile strength. It is, therefore, preferable to define the sampling frequency n' between $10^1$ and $10^4$ though it is variable according to the thickness of a sample layer to be analyzed. Assuming that ne denotes the number of elements to be analyzed, n' can be derived by the foregoing operational expression (7) as follows.

$$n' = ts/ne \cdot \Delta t \tag{8}$$

By the expression (8), the analysis time ts can be derived as follows.

$$ts = ne \cdot \Delta t \cdot n' \quad (9)$$

Since ts given by the expression (6) is equal to ts given by the expression (9), the following relation is established.

$$K \cdot x \cdot y \cdot z / I_1 = ne \cdot \Delta t \cdot n' \quad (10)$$

From the expression (10), $I_1$ can be derived as follows.

$$I_1 = K \cdot x \cdot y \cdot z / ne \cdot \Delta t \cdot n' \quad (11)$$

If two or more elements are to be analyzed, it is necessary to convert the analysis conditions of the secondary ion mass spectrometer at each sampling. The sampling time $\Delta t$ is therefore influenced by the time consumed in converting the analysis conditions. It results in defining the sampling time $\Delta t$ as a sum of a detecting time of the secondary ions and a time required for selectively switching a ratio of mass to charges in the secondary ion mass spectrometer. The sampling frequency n' may be a function of a thickness z of the sample layer to be analyzed. Moreover, for certain samples to be analyzed, it is possible to fix it as an optional value. Assuming that $\Delta t$, n' and K' are constant, the expression (11) can be transformed into $$I_1 = K' \cdot x \cdot y \cdot z / ne \quad (12)$$

As will be shown from the expression (12), $I_1$ can be derived by substitution values for x, y, z, and ne. In this case, the expressions and constants are stored in the storage unit 17.

Figure 3A:
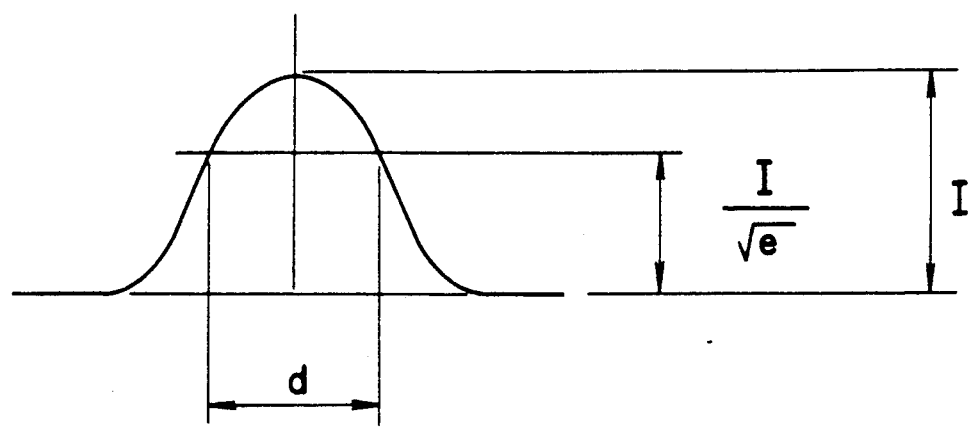
FIG. 3A is a chart illustrating current strength distribution of an ion beam.
Figure 3B:
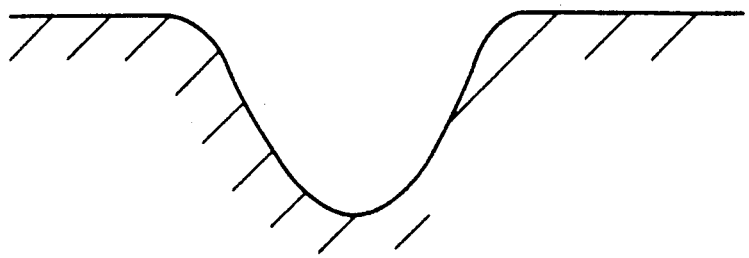
FIG. 3B is an illustration showing a sputtering crater formed on a sample in correspondence with the current strength distribution of the ion beam.
Figure 4A:
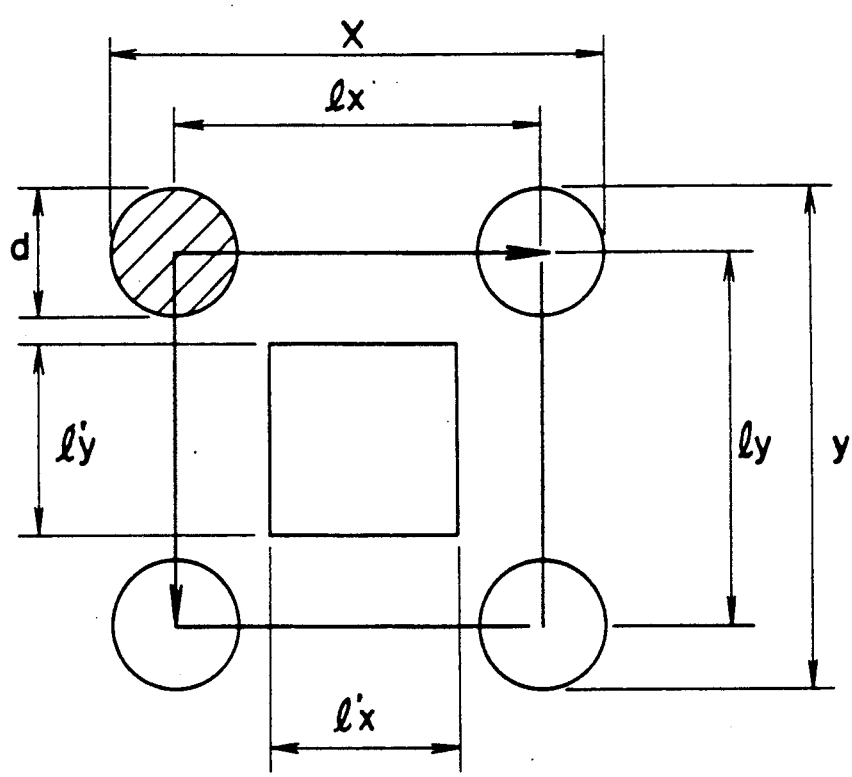
FIG. 4A is a view illustrating a scanned beam.
Figure 4B:
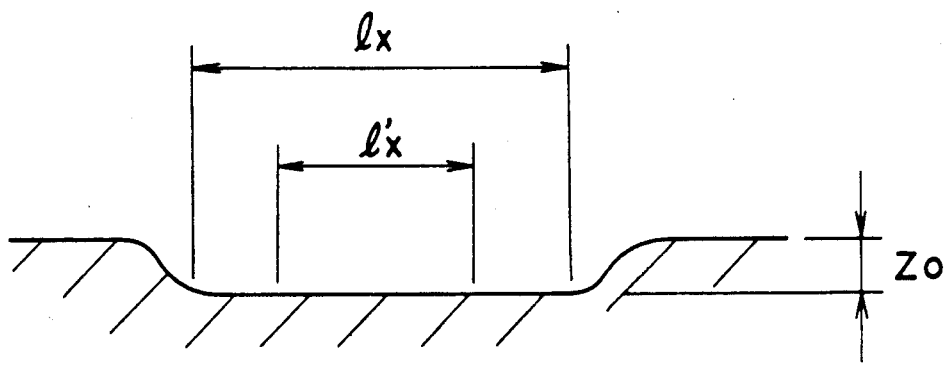
FIG. 4B is a view illustrating a sputtering state of a sample in correspondence with the beam.

The current strength distribution of the primary ion beams, on the other hand, is Gaussian distribution with a beam diameter d as shown in FIG. 3A. By sputtering the sample using the beam with this diameter d, a sputtering crater is formed along the Gaussian distribution as shown in FIG. 3B. The secondary ions ejected from the inside wall of the crater contain the other ions ejected from another vertical profile. This fact lowers a vertical resolution. The raster scan with horizontal lx and vertical ly on the sample surface plane as shown in FIG. 4A results in making the central area of the raster analogous in depth and forming the analogous sputter formed on the area. It means that the vertical resolution is improved. For detecting the secondary ions only from the area of lx' and ly' of the scan raster, the well-known electronic aperture method is employed. The values of lx and ly can be automatically arranged by inputting the values x and y into the input unit 16. Assuming that a beam diameter is d, the relation between x, y and lx, ly can be represented by the following expressions.

$$x = lx + d$$

$$y = ly + d$$

Further, assuming that the beam diameter d is represented by $$d = k \cdot lx \quad (13-1)$$

and k is a constant of 0.1 to 0.25, the value of x can be transformed as $$x = lx + k \cdot lx$$
$$= lx(l + k)$$

From this expression, $(1+k) = 1.1$ to $1.25$ can be derived. Hence, lx and d are represented by the following expressions.

$$lx = x/(l+k) \quad (13-2)$$

$$d = k/(l+k) \cdot x \quad (13-3)$$

Further, the dimensions of the uniform area, that is, the apertures lx' and ly' are represented by the following expression.

$$lx' = k' \cdot lx$$

$$ly' = k' \cdot ly \quad (14)$$

wherein k is a constant ranging from 0.01 to 0.25.

As described above, using the expressions (6), (11), (13-3), and (14), it is possible to derive the analysis conditions having the primary ion beam current $I_1$, the time ts required for sputtering the overall analytical area with the current $I_1$, the primary ion beam diameter d, and the sputter areas lx' and ly'.

Figure 6:
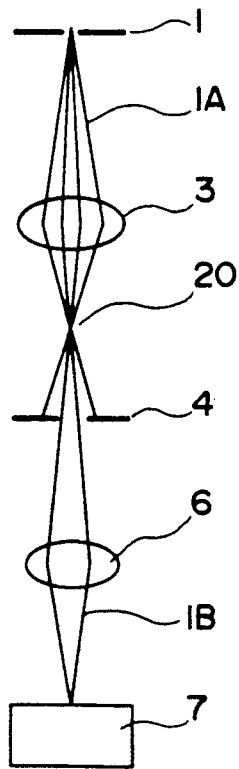
FIG. 6 is a view showing arrangement of a focusing system.
Figure 7:
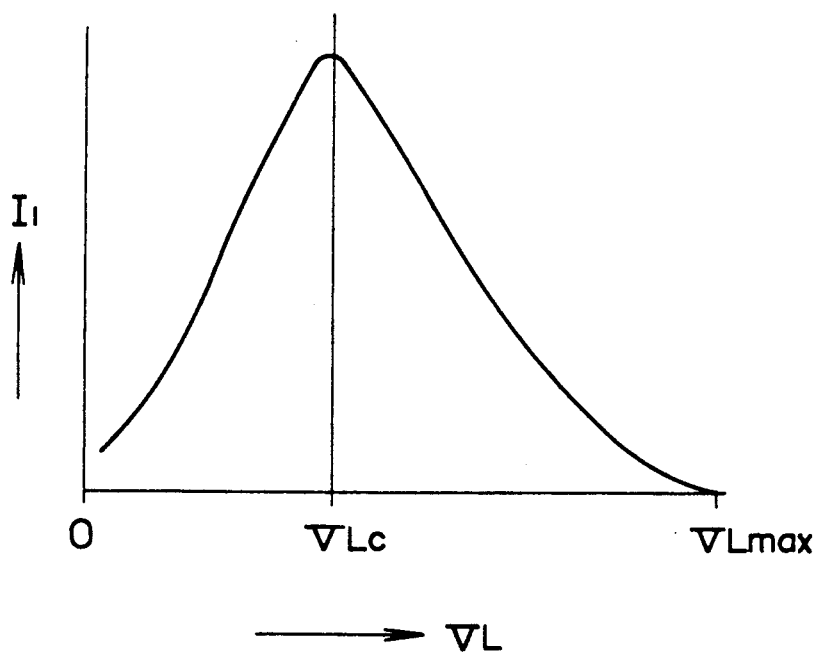
FIG. 7 is a chart illustrating relation between primary ion current and condenser lens voltage.

Next, how to set the conditions using the derived results will be described. FIG. 6 illustrates a focusing system in which the ion beam 1A is focused. As a higher voltage is applied to the condenser lens 3, the focusing point 20 come closer to the lens 3 and vice versa. By changing the application voltage, therefore, the quantity of ions passed through the objective aperture 4 is variable. It means that the condenser lens voltage $V_L$ and the primary current $I_1$ on the sample have such relation that the primary ion current has a maximum value when the condenser lens voltage reaches a value of $V_{LC}$ as shown in FIG. 7. In the range having a maximum value, it is quite difficult to control the condenser lens voltage. By superimposing a variable voltage on a fixed or half-fixed voltage being lower than $V_{LC}$, therefore, the condenser lens voltage $V_L$ can be adjustably controlled in the range of $V_{LC}$ to $V_{Lmax}$. The control operation is done by the condenser lens power source 10, the circuit of which is shown in detail in FIG. 8.

Figure 8:
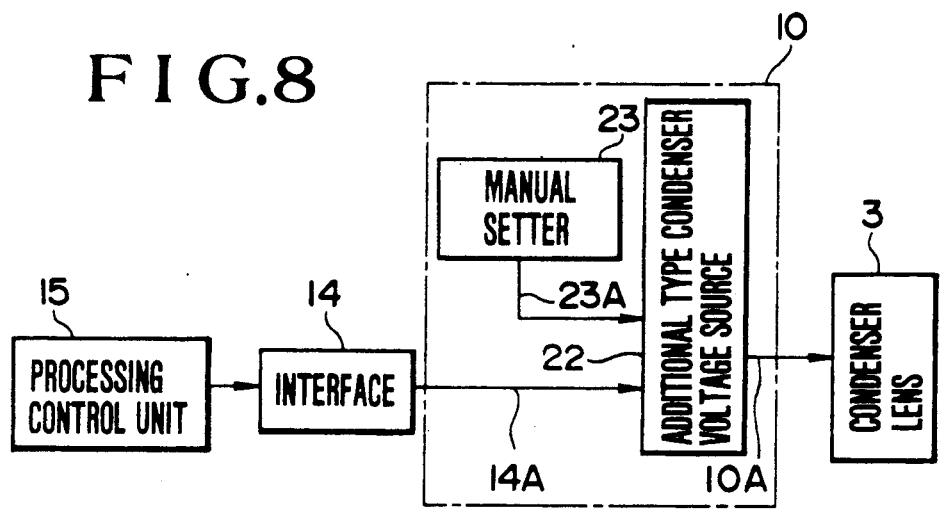
FIG. 8 is a block diagram showing arrangement of a voltage control circuit of the condenser lens.

In FIG. 8, 23 denotes a manual setter which is used for setting a fixed or half-fixed voltage being lower than $V_{LC}$. 17 denotes a storage unit which serves to store as a table the character in the range of $V_{LC}$ to $V_{Lmax}$ shown in FIG. 7. 15 denotes a processing control unit, which serves to read a voltage value along the primary ion current $I_1$ and output it as the control signal 14A through the interface 14. 22 denotes an addition type condenser voltage source 22, which serves to add an output signal 23A of the manual setter 23 to the control signal 14A and apply the resulting voltage, that is, a driving voltage 10A to the condenser lens 3.

If two or more samples are automatically and continuously analyzed, it is necessary to locate these samples on the sample stage 19. The analysis time of the sample employs a ts value defined by the expression (6). After passing a ts time when the first sample is analyzed, the processing control unit 15 serves to send the fine adjustment signal 14D to the sample stage power source 13 through the interface 14 so that the sample stage 19 is travelled for allowing the next sample to be analyzed.

Next, how to set the conditions of the primary ion beam focused system will be described.

As mentioned above, if the hole diameter of the objective aperture 4 remains fixed, the primary ion beam current $I_1$ depends on the application voltage $V_L$ of the condenser lens 3.

Assuming that $V_{LC}$ is a half-fixed voltage and $V_x$ is a variable voltage in the $V_L-I_1$ characteristic shown in FIG. 7, the application voltage $V_L$ can be derived as follows.

$$V_L = V_{LC} + V_x = f(I_1) \quad (15)$$

From the expressions (12) and (15), the variable voltage $V_x$ can be represented as follows.

$$V_x = f(I_1) - V_{LC} = f(K' \cdot x \cdot y \cdot z / ne) \quad (16)$$

In the expression (16), the function f $(K' \cdot x \cdot y \cdot z/ne)$ indicates the $V_L-I_1$ characteristic between $V_{LC}$ and $V_{Lmax}$. In actual, a characteristic table is created and stored in the storage unit 17. $V_x$ in the expression (16) is considered as the driving voltage 10A.

As will be understood from the above description, by inputtin x, y, z, ne (A, B), the application voltage $V_L$ of the condenser lens 3 is defined according to the expression (11) and is actually applied to the condenser lens 3, resulting in generating the primary ion beam current $I_1$.

Figure 9:
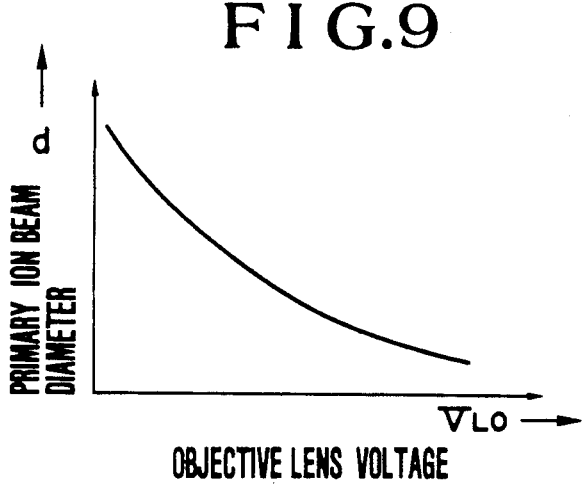
FIG. 9 is a chart illustrating relation between primary ion current and objective lens voltage.

Next, how to set the driving voltage 12A or the control signal 14C of the objective lens 6 will be described. When the application voltage VL of the condenser lens 3 is defined by the expression (16), the primary ion beam diameter d and the voltage $V_{L0}$ of the objective lens 6 have the following relation as shown in FIG. 9.

$$V_{L0} = f(d) = f(k \cdot lx) \quad (17)$$

If the scan width lx is defined, $V_{L0}$ can be set by the expression (17).

Figure 10:
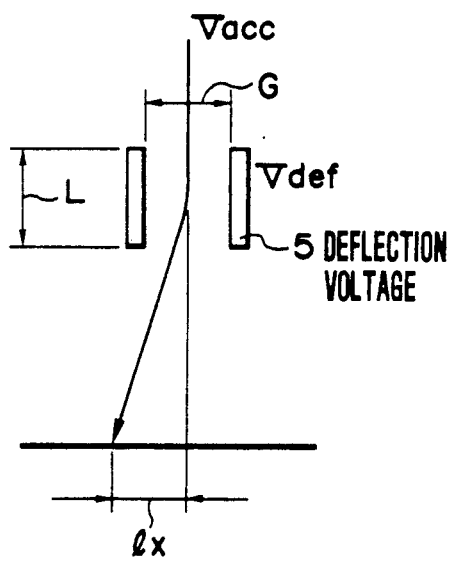
FIG. 10 is a view illustrating relation between a deflected electrode and deflection quantity.

Then, as shown in FIG. 10, an application voltage $V_{dEf}$ of the deflection electrode 5 will be described.

Assuming that the deflection electrode 5 employs an electrostatic parallel tabular type, the electrode length is L, the electrode interval is G, and the accelerating voltage of the primary ion beam is $V_{acc}$, on the condition that the deflection is equal to the scan width lx, the deflection lx and the application voltage $V_{dEf}$ have the following relation.

$$lx = (L/V_{acc} \cdot G) \cdot V_{dEf} \quad (18)$$

Thus, $$V_{dEf} = (V_{acc} \cdot G/L) \cdot lx \quad (19)$$

From the expression (19), by fixing the accelerating voltage $V_{acc}$, the deflection voltage $V_{dEf}$ is proportional to the deflection (analytical area) since G and L are fixed. $V_{dEf}$ employs the signal 14C or the voltage 12A. By substituting a value for lx, therefore, $V_{dEf}$ can be defined by the expression (19).

Figure 11:
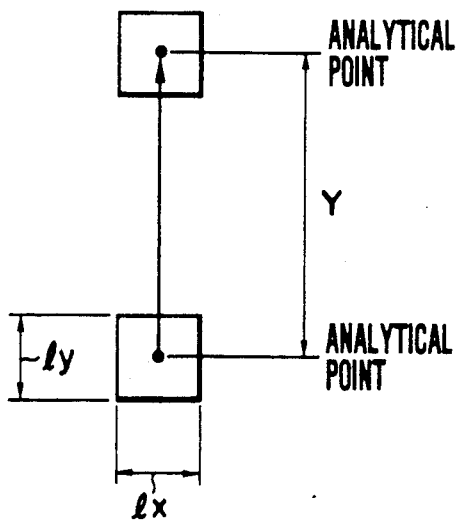
FIG. 11 is a view illustrating how to displace a sample surface to be analyzed.

When two or more areas on the sample 7 are automatically and continuously analyzed as fine adjusting the sample 7, assuming that the sample stage is driven by a pulse motor, the following relation is established.

$$N_p = k' \cdot y \quad (20)$$

where $N_p$ denotes a number of driving pulses and Y denotes movement as shown in FIG. 11, and k' is a constant, actually, an inverse of movement per unit pulse.

Figure 12:
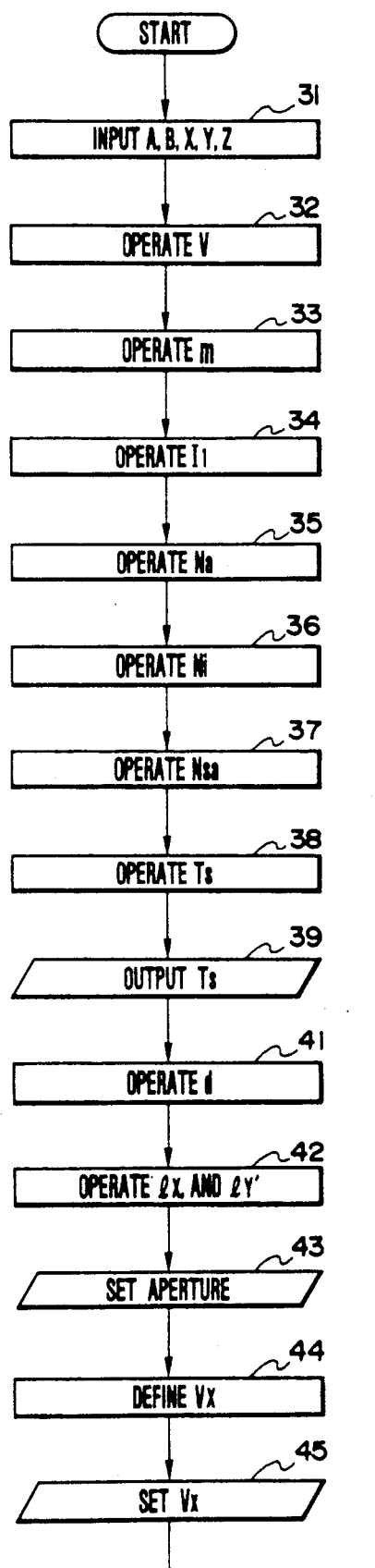
FIG. 12 is a flowchart illustrating the overall operation of an apparatus according to the invention.
Figure 12:
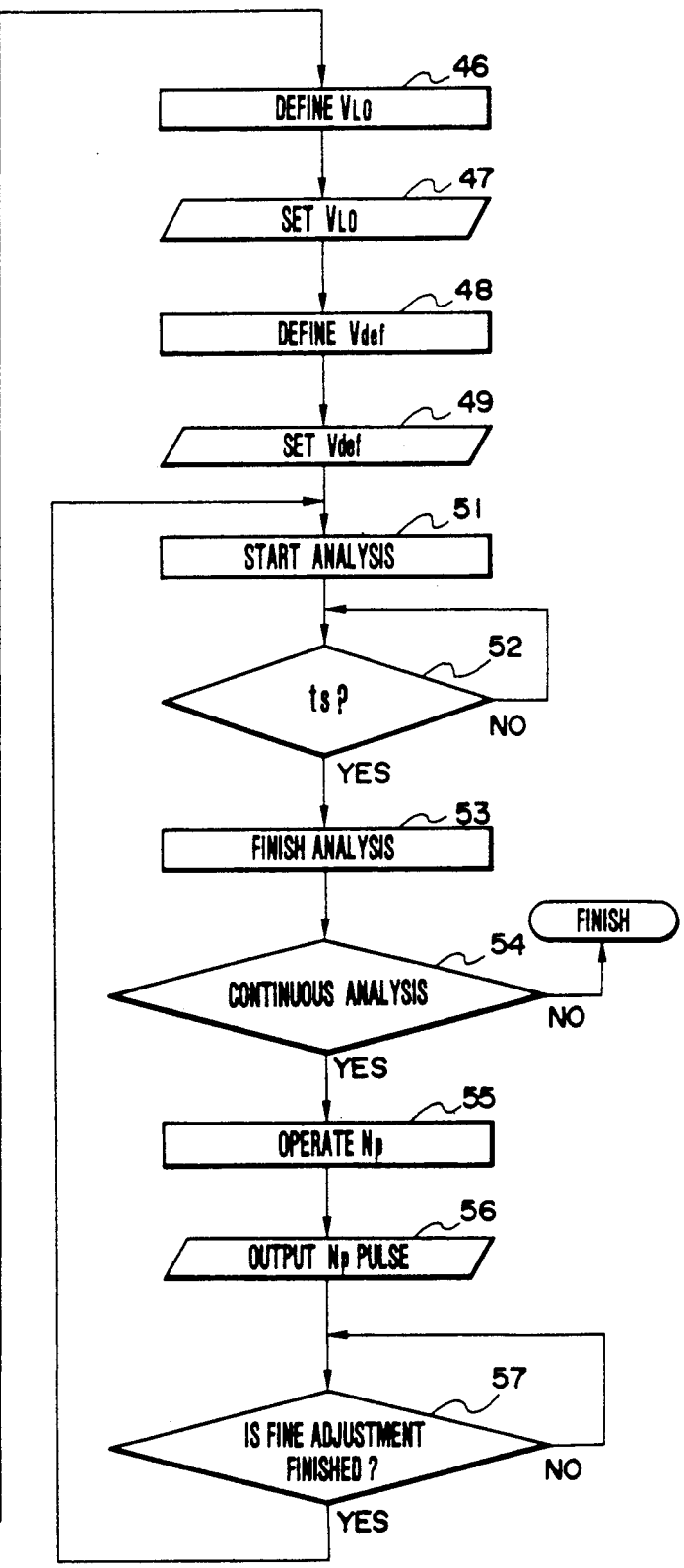

Next, the procedure of the processing control unit 15 shown in FIG. 1 will be described with reference to FIG. 12.

At a start step, the output unit 18 represents an input command for necessary data. At a step 31, the element names A and B and the analytical areas x, y, z are entered from the input unit 16 in accordance with the command. At a step 32, a volume V of the analytical area is derived from the expression (1). At a step 33, a weight m of the analytical area is derived from the expression (2). At a step 34, the primary ion beam current $I_1$ is derived from the expressions (11) and (12). At a step 35, the atom sum Na of the matrix element A contained in the analytical area is derived from the expression (3) as referencing the necessary data read from the storage unit 17. Further, at a step 36, how many ions are radiated on the sample surface per unit time is derived from the expression (4). At a step 37, the sputtering yield Sy of the element A is read from the storage unit 17 and the number of atoms Nsa to be sputtered per unit time is derived from the expression (5). At a step 38, the analysis time ts required for sputtering the overall analytical area is derived from the expression (6). And at a step 39, the time ts is displayed on the output unit 18.

Next, at a step 41, the primary ion beam diameter d is derived from the expression (13-3). At a step 42, the apertures lx' and ly' are derived from the expressions (13-2) and (14). Then, at a step 43, the derived apertures are set. It means that the detected signal 9A of the mass spectrometer 9 is gated through the interface 14. In general, this is a known method.

At a step 44, using the ion current $I_1$ derived at the step 34 and the data input from the input unit 16, the variable voltage $V_x$ is derived from the expression (16). At a step 45, this voltage $V_x$ is set as a driving voltage supplied from the condenser lens power source 10 to the condenser lens 3.

At a step 46, the voltage $V_{L0}$ applied on the objective lens 6 is read from the characteristic table shown in FIG. 9, which is stored in the storage unit 17 on the ion beam diameter d derived at the step 41. At a step 47, this voltage $V_{L0}$ is set to the objective lens power source 12.

At a step 48, the deflection voltage $V_{dEf}$ is derived from the expression (19). Then, at a step 49, this voltage $V_{dEf}$ is set to the deflection power source 11.

After the foregoing setting is finished, at a step 51, the analyzing operation is started. Then, at a step 52, the operation is kept until the analysis time ts passes. After the analysis time ts has passed, the operation finishes at a step 53. Next, at a step 54, it is checked if there is left a sample to be continuously analyzed. If not, the analysis completely finishes. If yes, at a step 55, the number of driving pulses $N_p$ used for moving the fine adjustment unit 19 is derived from the expression (20). At a step 56, the $N_p$ pulses are supplied to the sample stage power source 13. At a step 57, it is assured that the sample stage 19 finishes its movement. Then, the procedure returns to the step 51 for analyzing a new sample.

As will be understood from the above description, the secondary ion mass spectrometry apparatus according to the invention can improve the analytical operation and the reproducibility of the data, because the operating control unit serves to derive the approximate analysis condition and the analysis time on which it is possible to set the primary ion current, the primary ion beam diameter, and the scan width by inputting the analytical element name and area to the input unit.

Moreover, since the analysis required time is derived and output on the basis of the input parameter and the set condition value, the present invention is capable of breaking down the restriction that more approximate output requires more working time of an operator.

I claim:

1. A secondary ion mass spectrometry apparatus serving to radiate a primary ion beam from an ion source to a sample to be analyzed through a focusing system and perform mass analysis of secondary ions ejected from the sample for analyzing an element contained in said sample, said secondary ion mass spectrometry apparatus comprising;
    an input unit for inputting data including at least an analytical element name and an analytical area,
    a storage unit for storing operational expressions operated on the data inputted from said input unit and tables to be referenced on at least either one of said input data and the results derived by said operational expressions and from which the necessary data is read thereon, and
    a control unit for setting focusing conditions of said focusing system by using the input data input from said input unit, said operational expressions and tables stored in said storage unit.

2. The secondary ion mass spectrometry apparatus as claimed in claim 1, wherein said focusing system includes a condenser lens for focusing said primary ion beam extracted from said ion source, a deflection electrode for deflecting said primary ion beam, and an objective lens for focusing said primary ion beam onto said sample.

3. The secondary ion mass spectrometry apparatus as claimed in claim 2, wherein said control unit includes means for setting a signal to be supplied to at least one of said condenser lenses, said deflection electrode, and said objective lens.

4. The secondary ion mass spectrometry apparatus as claimed in claim 3, wherein said control unit includes a condenser lens voltage control means for controlling said primary ion beam current by controlling a condenser lens voltage to be supplied to said condenser lens.

5. The secondary ion mass spectrometry apparatus as claimed in claim 4, wherein said condenser lens voltage control means comprises;
    means for operating a current value of said primary ion beam on said input data,
    means for defining said condenser lens voltage on the operational result of said current operating means, and
    means for supplying said voltage defined by said defining means to said condenser lens.

6. The secondary ion mass spectrometry apparatus as claimed in claim 5, wherein said current value operating means is means for deriving said primary ion beam current on said input data from said input unit using the operational expressions stored in said storage unit.

7. The secondary ion mass spectrometry apparatus as claimed in claim 5, wherein said voltage defining means is means for defining said condenser lens voltage on the current value derived by said current value operating means by referencing the table stored in said storage unit.

8. The secondary ion mass spectrometry apparatus as claimed in claim 7, wherein said storage unit stores as a table the relation between said primary ion beam current and said condenser lens voltage for condenser lens voltage larger than a voltage realizing a maximum value of said primary ion beam current, and
    said voltage defining means includes means for setting a voltage being equal to said condenser lens voltage realizing the maximum value of said primary ion beam current, means for reading a larger voltage than said condenser lens voltage matching to said maximum value from the table about the relation between said condenser lens voltage and said primary ion beam current stored in said storage unit, based on said current value derived from said current value operating means, and means for adding said read voltage into said voltage set by said voltage setting means and supplying the adding result to said condenser lens.

9. The secondary ion mass spectrometry apparatus as claimed in claim 3, wherein said control unit includes means for setting a deflection voltage to be supplied to said deflection electrode based on said input data.

10. The secondary ion mass spectrometry apparatus as claimed in claim 3, wherein said control unit includes means for operating an objective lens voltage based on said input data and supplying said objective lens voltage to said objective lens.

11. The secondary ion mass spectrometry apparatus as claimed in claim 1 further comprising means for locating two or more samples and serially moving one of said samples to a position on which said primary ion beam is radiated.

12. The secondary ion mass spectrometry apparatus as claimed in claim 1 further comprising;
    means for operating said primary ion beam current based on the input data from said input unit using the operational expressions stored in said storage unit,
    means for deriving a sputtering time of said analytical area based on said primary ion beam current derived in said current operating means and said input data from said input unit using the operational expressions stored in said storage unit, and
    output means for representing the time derived in said deriving means.

* * * * *